(12) United States Patent
Alpegiani et al.

(10) Patent No.: US 9,340,571 B2
(45) Date of Patent: May 17, 2016

(54) PROCESS FOR THE PURIFICATION OF ABIRATERONE ACETATE

(71) Applicant: OLON S.P.A., Rodano (IT)

(72) Inventors: Marco Alpegiani, Rodano (IT); Tania Cristiano, Milan (IT); Eugenio Cucchetti, Rodano (IT)

(73) Assignee: OLON S.P.A., Rodano (MI) (IT)

( * ) Notice: Subject to any disclaimer, the term of this patent is extended or adjusted under 35 U.S.C. 154(b) by 0 days.

(21) Appl. No.: 14/436,527

(22) PCT Filed: Oct. 21, 2013

(86) PCT No.: PCT/EP2013/071930
§ 371 (c)(1),
(2) Date: Apr. 17, 2015

(87) PCT Pub. No.: WO2014/064032
PCT Pub. Date: May 1, 2014

(65) Prior Publication Data
US 2016/0052958 A1      Feb. 25, 2016

(30) Foreign Application Priority Data
Oct. 22, 2012   (IT) .......................... MI2012A001788

(51) Int. Cl.
*C07J 43/00*      (2006.01)
*B01D 15/32*      (2006.01)

(52) U.S. Cl.
CPC ............. *C07J 43/003* (2013.01); *B01D 15/327* (2013.01)

(58) Field of Classification Search
None
See application file for complete search history.

(56) References Cited

FOREIGN PATENT DOCUMENTS

| CN | 101 768 199 | 7/2010 |
|---|---|---|
| CN | 102 030 798 | 4/2011 |
| WO | 9509178 | 4/1995 |
| WO | 2013053691 | 4/2013 |

OTHER PUBLICATIONS

Potter, et al., "A Convenient, Large-Scale Synthesis of Abiraterone Acetate A3.Beta-Acetoxy-17-(3-Pyridyl) Androsta-5,16-Dieneu, A Potential New Drug for the Treatment of Prostate Cancer", Organic Preparations and Procedures International, Organic Preparation and Procedure Co, Newton Highlands, MA, U.S., vol. 29, No. 1, Jan. 1, 1997, pp. 123-128.
International Search Report and Written Opinion of PCT/EP2013/071930 of Feb. 4, 2014.
International Preliminary Report on Patentability of PCT/EP2013/071930 of Nov. 5, 2014.

*Primary Examiner* — Zinna Northington Davis
(74) *Attorney, Agent, or Firm* — Silvia Salvadori, P.C.; Silvia Salvadori

(57) ABSTRACT

The invention relates to a process for the purification of crude abiraterone acetate by treatment with polymer resins in aqueous solvent. The purified product is recovered by simple concentration and filtration.

8 Claims, No Drawings

PROCESS FOR THE PURIFICATION OF ABIRATERONE ACETATE

This application is a U.S. national stage of PCT/EP2013/071930 filed on 21 Oct. 2013, which claims priority to and the benefit of Italian Application No. MI2012A001788 filed on 22 Oct. 2012, the contents of which are incorporated herein by reference in their entireties.

The invention relates to a process for the purification of crude abiraterone acetate by treatment with polymer resins in aqueous solvent. The purified product is recovered by simple concentration and filtration.

BACKGROUND TO THE INVENTION

Abiraterone acetate, the chemical name of which is (3β)-17-(3-pyridinyl) androsta-5,16-dien-3-yl acetate, is the prodrug of the active metabolite abiraterone, a selective inhibitor of the enzyme CYP17.

Abiraterone acetate is the active ingredient of a novel medicament for the treatment of prostate carcinoma in adult men.

The preparation of abiraterone acetate was originally disclosed in EP0633893.

The synthesis scheme involves the conversion of dehydroepiandrosterone-3-acetate (I) to the corresponding enol triflate (II) by treatment with trifluoromethanesulphonic anhydride and 2,6-di-tert-butyl-4-methylpyridine.

The Suzuki reaction between 3β-acetoxyandrosta-5,16-dien-17-yl trifluoromethanesulphonate (II) and diethyl(3-pyridyl)borane affords crude abiraterone acetate which is purified by silica gel chromatography, eluting with a mixture of ethyl ether and petroleum ether, and finally crystallised from hexane.

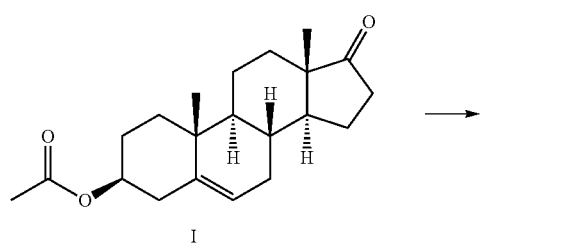

I

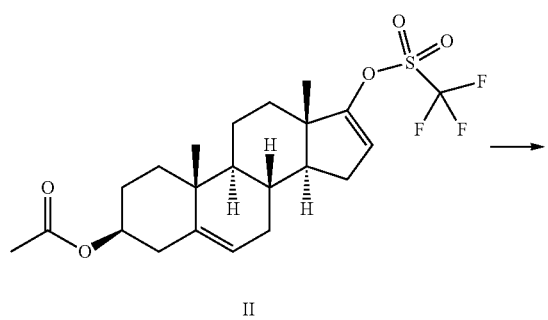

II

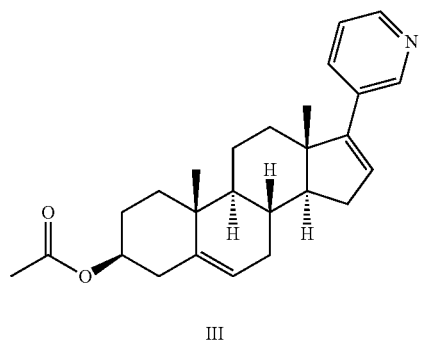

III

The crude abiraterone acetate obtained under said conditions contains substantial amounts of the following impurity (IV), deriving from the elimination of acetic acid in the presence of 2,6-di-tert-butyl-4-methylpyridine [*Journal of Medicinal Chemistry* 38, 2463-2471 (1995)]

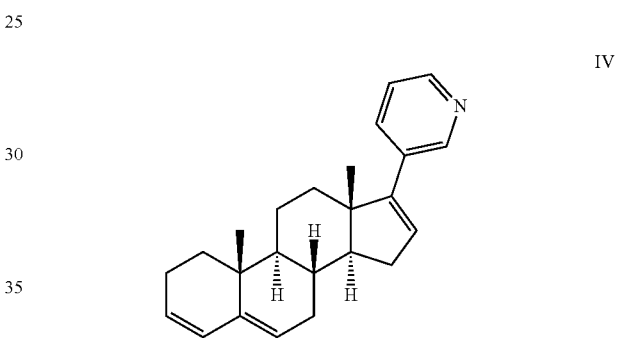

IV

The use of more common, cheaper bases of 2,6-di-tert-butyl-4-methylpyridine is claimed in patent application WO2006/021777 (see also EP1781683 and U.S. Pat. No. 8,236,946); above all the formation of impurity IV is avoided by using said bases, although the intermediate II formation reaction is not complete, and the crude abiraterone acetate obtained after the Suzuki reaction contains appreciable amounts of dehydroepiandrosterone-3-acetate (I). Said crude product can be purified by salification of III with methanesulphonic acid (WO2006/021776, see also EP1789432 and U.S. Pat. No. 8,076,474); however, the purity of the mesylate thus obtained is not very high, even after recrystallisation from isopropyl alcohol (purity of crude product <90%, purity of purified product about 96%), and the overall yield is rather poor.

A sequence comprising purification of crude product III via formation of the salt with sulphuric acid, reconversion to III and final crystallisations from dichloromethane/petroleum ether and ethanol/water, is disclosed in IPCOM000211139D. The yields and quality of the products obtained are not reported, and treatment with acetic anhydride/DMAP is performed before the final crystallisations.

An alternative process for the preparation of abiraterone acetate is disclosed in EP0721461.

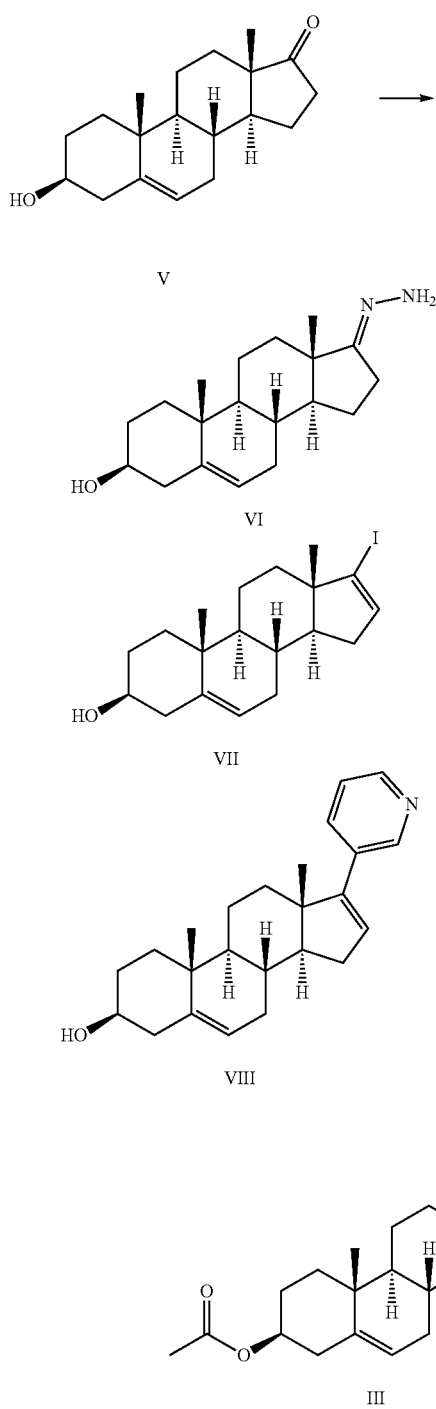

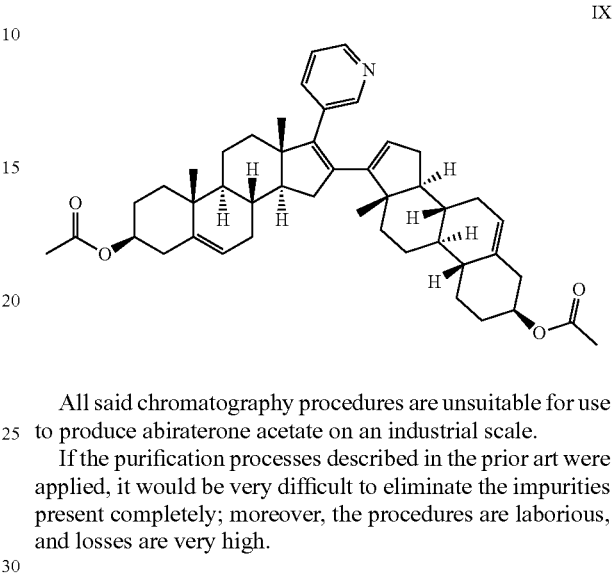

The key intermediate of this process is 17-iodo-androsta-5,16-dien-3β-ol VII, obtained in two steps from dehydroepiandrosterone V via hydrazone VI. The Suzuki reaction between vinyl iodide VII and diethyl(3-pyridyl)borane affords abiraterone VIII, which is then acetylated to give abiraterone acetate III.

The process is described in detail in *Organic Preparations and Procedures International* 29, 123-128 (1997).

As in the case of the synthesis process illustrated in the previous scheme, this process also requires an elaborate procedure for the purification of crude abiraterone acetate, which comprises (see the publication cited above) one direct-phase (silica) chromatography step and one reverse-phase (LiChroprep® RP-8) chromatography step, together with repeated crystallisations from organic solvents. This elaborate purification procedure is mainly required to remove a critical impurity that forms during synthesis of VIII by Heck-type reaction between VII and VIII, to give "dimer" IX after acetylation.

All said chromatography procedures are unsuitable for use to produce abiraterone acetate on an industrial scale.

If the purification processes described in the prior art were applied, it would be very difficult to eliminate the impurities present completely; moreover, the procedures are laborious, and losses are very high.

DESCRIPTION OF THE INVENTION

We have now surprisingly found that abiraterone acetate can be obtained with high yields and high purity by a low-cost purification process which is easily implemented on an industrial scale.

The present invention provides a process for the purification of abiraterone acetate from crude products, regardless of the synthesis process used for their preparation; the process comprises preparation of a solution of crude product, adsorption on a polymer resin and elution of abiraterone acetate from the resin using a mixture of water and a polar solvent as eluent.

In the process according to the invention, crude abiraterone acetate has a purity generally ranging between 50 and 95%. The product obtained after purification has a purity above 99.5%, and the impurities present after purification do not exceed 0.10% each. Moreover, said purification process according to the invention removes heavy metals very efficiently, and the palladium used to obtain crude abiraterone acetate (which is present in substantial amounts in the crude product) is undetectable in abiraterone acetate purified according to the invention.

The purification technique preferably used is hydrophobic interaction chromatography. The resins can have an acrylic or styrene-divinylbenzene matrix, and have no functional groups.

For example, Diaion HP or SP resins (Mitsubishi) or Amberlite XAD (Rohm and Haas) can be used.

The resin used can have a particle-size distribution ranging between 50 and 600 μm, preferably between 60 and 200 μm.

The resins used can easily be regenerated and equilibrated for multiple cycles, with no need to remove them from the column. They can also be used for a very large number of cycles, without significantly reducing their selective capacity.

The crude abiraterone acetate is typically dissolved in the minimum amount of an organic solvent such as methanol, ethanol, isopropanol, n-propanol, acetonitrile, dimethyl sulphoxide, tetrahydrofuran or acetone, or in a mixture of organic solvent with water. The final concentration of the crude product preferably ranges between 10 and 200 mg/mL. The dissolution temperature preferably ranges between 15 and 40° C.

Any insoluble materials can be removed by filtration.

Crude abiraterone, solubilised as described above, is loaded into a column containing resin equilibrated with a mixture of organic solvent/water or organic solvent/aqueous buffer, to allow the formation of hydrophobic bonds between the product and the resin.

The amount of product loaded can be between 5 and 50 grams per liter of resin, preferably between 10 and 30 grams per liter of resin.

The solvent used can be, for example, methanol, isopropanol, ethanol, acetonitrile or acetone, or a mixture thereof.

When aqueous buffers are used, the aqueous solution will preferably contain alkaline metal or ammonium salts of inorganic acids such as phosphoric acid, or of carboxylic acids such as formic acid or acetic acid, or other salts such as tris-(2-hydroxymethyl)-aminomethane hydrochloride (TRIS-HCl). The molarity of the buffer solutions can range between 10 and 300 mM, preferably between 10 and 100 mM.

The solvent concentration in the starting mixture must be such as to allow the formation of hydrophobic bonds between the product and the resin, and generally ranges between 30 and 80%.

The elution (in isocratic or gradient mode) is preferably performed with mixtures at increasing solvent concentrations.

The elution rate can range between 0.5 and 2.0 volumes of solvent to volume of resin per hour.

The eluate is typically collected in fractions and analysed by a suitable analysis technique such as TLC, GC or HPLC, to establish the procedure for collection of the fractions containing abiraterone with a high degree of purity, and optionally the fractions containing significant impurities.

Under the optimum operating conditions, the fractions of abiraterone acetate with high purity are usually collected after 4-8 bed volumes of eluent mixture.

The entire chromatography process, including regeneration of the resin, typically requires 6 to 12 bed volumes of eluent.

The fractions containing abiraterone acetate with a purity above 99.5% are concentrated under vacuum to a residual volume amounting to 5-40% of the initial volume. In this way the solvent is partly or totally removed and the abiraterone acetate is insolubilised in the remaining aqueous phase.

The product is then recovered by filtration or centrifugation, and the crystals are washed with a minimal amount of water.

The product loss in the mother liquor is usually below 1%.

The product can be dried under vacuum at a temperature generally ranging between 30 and 60° C.

Typically, a white crystalline product is obtained, with an HPLC purity ranging between 99.5 and 99.8% and an assay above 99%.

The resins used for the purification to which the present patent application relates can be reused numerous times. It is not necessary to regenerate the resin after each chromatography run. The resin can easily be regenerated in accordance with the manufacturer's instructions after a given number of cycles.

The process will now be further illustrated by the following examples.

Example 1

Synthesis of Crude Abiraterone Acetate Via Vinyl Triflate II

Trifluoromethanesulphonic anhydride (137 mL) and picoline (75 mL) in methylene chloride (2.5 L) are added in sequence to a solution of prasterone acetate (250 g) in methylene chloride (2.5 L), maintaining the temperature at between −5° C. and 0° C., and left under stirring for about 2 h. After adding cold water (3.7 L; 0-2° C.) without exceeding the temperature of 10° C., the organic phase is separated and washed with a cold aqueous solution of 2N HCl and then with aqueous sodium chloride. The mixture is then concentrated under vacuum, to obtain an oily residue (about 340 g).

The crude vinyl triflate thus obtained (about a 4:1 mixture of vinyl triflate and prasterone acetate) is taken up with tetrahydrofuran (3.7 L). Diethyl(3-pyridyl)borane (90 g), bis(triphenylphosphine)palladium II chloride (3.8 g) and a 2M sodium carbonate aqueous solution (1 L) are loaded under inert gas environment. The resulting mixture is refluxed for about 1 h, then cooled to room temperature, and ethyl acetate (2.5 L) and water (2.5 L) are added. The aqueous phase is back-extracted with ethyl acetate (1.4 L), the combined organic phases are treated with decolourising carbon (about 100 g), and then concentrated under vacuum to obtain crude abiraterone acetate as an oil (320 g; purity about 87%; assay 51%).

Example 2

Synthesis of Crude Abiraterone Acetate Via Vinyl Iodide VII

17-Iodoandrosta-5,16-dien-3β-ol [Organic Preparations and Procedures Int., 29, 123-134 (1997)] (90 g) in tetrahydrofuran (1.0 L), in an inert gas environment, is added with diethyl(3-pyridyl)borane (40 g), bis(triphenylphosphine)palladium II chloride (1.5 g) and a 2M sodium carbonate aqueous solution (450 mL). The resulting mixture is refluxed until the reaction is complete (about 50 h), then cooled to room temperature, and tetrahydrofuran (1 L) is added. The organic phase is separated and washed with a 5% sodium chloride aqueous solution, then dried over magnesium sulphate. The residue is then concentrated under vacuum, and the concentrate is taken up in tert-butyl methyl ether (about 600 mL) to obtain a sandy solid, which is isolated by filtration (at 0-5° C.) and dried under vacuum at 40° C. for 16 h.

The crude abiraterone thus obtained (about 64 g) is taken up in methylene chloride (350 mL), and the resulting mixture, cooled to a temperature of −5 to 0° C., is added with acetic anhydride (130 mL) and then with triethylamine (190 mL), maintaining the temperature at −5 to 0° C. The mixture is stirred at room temperature for about 25 h, then washed with water and concentrated under vacuum, taking up the residue in acetone (250 mL). The resulting solid is isolated by filtration (at 0-5° C.) and dried under vacuum at 40° C. for 16 h (about 46 g; purity: 82.5%; assay: about 73%). A second fraction of crude abiraterone acetate, as an oil, is obtained by concentration of the mother liquor under vacuum (54 g, purity: 74%, assay: about 45%).

Example 3

Synthesis of Crude Abiraterone Acetate Via Vinyl Triflate II

Trifluoromethanesulphonic anhydride (235 g) is dropped into a solution of prasterone acetate (250 g) in methylene chloride (5 L), maintaining the temperature between −5° C. and 0° C., and anhydrous sodium carbonate (80 g) is added in portions. The mixture is stirred for 4 h at 0-5° C. Cold water (2.5 L) is added and the organic phase is separated and washed with a 10% sodium chloride aqueous solution. The mixture is treated with decolourising carbon (120 g), and then concentrated under vacuum to obtain an oily residue (about 355 g). The vinyl triflate thus obtained is taken up with tetrahydrofuran (3.0 L), and diethyl(3-pyridyl)borane (100 g), bis(triphenylphosphine)palladium II chloride (3.3 g) and a 2M sodium carbonate aqueous solution (900 mL) are loaded in succession in an inert gas environment. The resulting mixture is refluxed for about 1 h, then cooled to room temperature, and ethyl acetate (2.5 L) and water (2.5 L) are added. The aqueous phase is back-extracted with ethyl acetate (1.4 L), and the combined organic phases are treated with decolourising carbon (about 100 g), and then concentrated under vacuum to obtain crude abiraterone acetate as an oil (304 g; purity about 92%; assay 52%).

Example 4

Synthesis of Crude Abiraterone Acetate Via Vinyl Triflate II

Trifluoromethanesulphonic anhydride (45.4 mL) is dropped into a solution of prasterone acetate (100 g) and 2,6-di-tert-butyl-4-methylpyridine (58 g) in methylene chloride (1 L) at −5° C., maintaining the temperature between −5° C. and 0° C. and stirring at said temperature for about 5 h. The mixture is then concentrated under vacuum, and the concentrate is taken up in n-hexane (about 1500 mL) to obtain a precipitate which is isolated by filtration. The filtered solution is washed with a 1N hydrochloric acid solution (about 1.5 L) and then with a sodium chloride saturated aqueous solution (500 mL). The organic phase is added with potassium carbonate (50 g), and the resulting suspension is stirred for about 15 h at room temperature, then filtered. After removal of the solvent under vacuum an oil (about 110 g) is obtained, which is taken up with tetrahydrofuran (1.5 L). The solution is degassed and diethyl(3-pyridyl)borane (54.5 g), bis(triphenylphosphine)palladium II chloride (1.8 g) and a 2M sodium carbonate aqueous solution (500 mL) are added in sequence in an inert gas environment. The resulting mixture is refluxed for about 1 h, then cooled to room temperature, and ethyl acetate (1 L) and water (1 L) are added. The aqueous phase is back-extracted with ethyl acetate (0.5 L), and the combined organic phases are concentrated under vacuum to obtain crude abiraterone acetate as oil (230 g; purity about 88%; assay 35%).

Example 5

Purification of Crude Abiraterone Acetate Obtained Via Vinyl Triflate II

Crude abiraterone acetate obtained as described in Example 1 (about 300 g) is dissolved in a mixture of IPA and acetonitrile and loaded onto a column packed with 9 liters of DIAION HP20ss resin (Mitsubishi) conditioned with a mixture of acetonitrile/IPA/ammonium acetate buffer.

The mixture is eluted with a mixture of acetonitrile/IPA/10 mM ammonium acetate buffer in the ratio of 68:2:30 (about 20 L), and then with an acetonitrile gradient (about 60 liters). The fractions containing the product with a purity above 99.5% (HPLC monitoring) are combined (total volume: about 25 L; abiraterone acetate content: about 125 g).

After concentration of the mixture, filtration, washing with water and drying (12 h, 40° C.), abiraterone acetate is obtained as a white crystalline solid (120 g; HPLC purity 99.6%).

[HPLC analysis method: Phenomenex Luna C8 column, 150×4.6 mm, 5 μm; a gradient is used wherein phase A consists of a 10 mM solution of ammonium acetate in $H_2O$ and phase B consists of acetonitrile containing 2% isopropanol; detection at 254 and 220 nm].

Example 6

Purification of Crude Abiraterone Acetate Obtained Via Vinyl Iodide VII

Crude abiraterone acetate obtained as described in Example 2 (100 g) is dissolved in a mixture of IPA and acetonitrile and the solution is loaded onto a column packed with 5 liters of DIAION HP20ss resin (Mitsubishi) equilibrated in acetonitrile/IPA/ammonium acetate buffer.

The column was eluted with acetonitrile/IPA/10 mM ammonium acetate buffer in a 78:2:20 ratio (about 20 L).

The fractions collected during elution were analysed by the HPLC process described above, and those containing abiraterone with a purity above 99.5% were combined and concentrated under vacuum. The resulting suspension was filtered and washed with water and the crystals were dried as described above, to obtain about 50 g of abiraterone acetate with an HPLC purity of 99.7%.

The main impurity present in the crude product, namely dimer IX, can be recovered by elution with acetonitrile/acetic acid 95:5.

Example 7

Purification of Crude Abiraterone Acetate Obtained Via Vinyl Triflate II

Crude abiraterone acetate, obtained as described in Example 3, is purified similarly to the procedure described in Example 5, and abiraterone acetate with a yield of 86% and an HPLC purity of 99.79% is obtained.

Example 8

Purification of Crude Abiraterone Acetate Obtained Via Vinyl Triflate II

Crude abiraterone acetate, obtained as described in Example 4, is purified similarly to the procedure described in Example 5, and abiraterone acetate with a yield of 91% and an HPLC purity of 99.55% is obtained.

Example 9

Purification of Crude Abiraterone Acetate Obtained Via Vinyl Triflate II

Crude abiraterone acetate obtained as described in Example 1 (HPLC purity of crude product: about 87%; abiraterone acetate content: about 500 g) is dissolved in a mixture of IPA and acetonitrile and loaded onto a column packed with 9 liters of DIAION HP20ss resin (Mitsubishi) conditioned with a mixture of acetonitrile/IPA/ammonium acetate buffer.

The mixture is eluted with a mixture of acetonitrile/IPA/10 mM ammonium acetate buffer in the ratio of 68:2:30 (about 20 L), and then with an acetonitrile gradient (about 60 liters). The fractions containing the product with a purity above 99.5% (HPLC monitoring) are combined (total volume: about 25 L; abiraterone acetate content: about 425 g).

After concentration of the mixture, filtration, washing with water and drying (12 h, 40° C.), abiraterone acetate is obtained as a white crystalline solid (420 g; HPLC purity 99.6%).

The invention claimed is:

1. A process for the purification of abiraterone acetate starting from crude products, which comprises
preparing a solution of the crude product, adsorbing it on a polymer resin and
eluting abiraterone acetate from the resin using a mixture of water/aqueous buffer and a polar solvent as eluent.

2. A process according to claim 1 wherein the polymer resin is a resin suitable for hydrophobic interaction chromatography.

3. A process according to claim 1 wherein the resins are selected from resins with an acrylic or styrene-divinyl benzene matrix free from functional groups.

4. A process according to claim 2 wherein the resin has a particle size distribution ranging from 50 to 600 µm.

5. A process according to claim 1 wherein the crude abiraterone acetate is dissolved in methanol, ethanol, isopropanol, n-propanol, acetonitrile, dimethylsulphoxide, tetrahydrofuran or acetone or in a mixture of said solvents with water.

6. A process according to claim 1 wherein the eluent used for eluting the resin is a mixture of water or aqueous buffering agents with one or more solvents selected from methanol, isopropanol, ethanol, acetonitrile, acetone or a mixture thereof.

7. A process according to claim 6 wherein the isocratic or gradient elution is carried out with mixtures with increasing solvent concentrations.

8. A process according to claim 4 wherein the particle size distribution is ranging from 60 to 200 µm.

* * * * *